(12) United States Patent
Shalaby

(10) Patent No.: US 6,503,991 B2
(45) Date of Patent: *Jan. 7, 2003

(54) COPOLYESTERS WITH MINIMIZED HYDROLYTIC INSTABILITY AND CRYSTALLINE ABSORBABLE COPOLYMERS THEREOF

(75) Inventor: Shalaby W. Shalaby, Anderson, SC (US)

(73) Assignee: Poly-Med, Inc., Anderson, SC (US)

(*) Notice: Subject to any disclaimer, the term of this patent is extended or adjusted under 35 U.S.C. 154(b) by 0 days.

This patent is subject to a terminal disclaimer.

(21) Appl. No.: 09/737,053

(22) Filed: Dec. 14, 2000

(65) Prior Publication Data

US 2001/0023279 A1 Sep. 20, 2001

Related U.S. Application Data

(62) Division of application No. 09/420,767, filed on Oct. 19, 1999, now Pat. No. 6,255,408.
(60) Provisional application No. 60/107,503, filed on Nov. 6, 1998.

(51) Int. Cl.[7] ........................ C08G 63/02; C08G 63/64; C08G 63/91
(52) U.S. Cl. ........................ 525/437; 525/411; 525/439; 528/302; 606/151; 606/154; 606/230
(58) Field of Search ................................ 525/437, 411, 525/439; 528/302; 606/151, 154, 230

(56) References Cited

U.S. PATENT DOCUMENTS

| | | | |
|---|---|---|---|
| 4,429,080 A | 1/1984 | Casey et al. | 525/415 |
| 4,532,928 A | 8/1985 | Bezwada et al. | 128/335.5 |
| 5,133,739 A | 7/1992 | Bezwada et al. | 606/230 |
| 5,236,444 A | 8/1993 | Muth et al. | 606/230 |
| 5,431,679 A | 7/1995 | Bennett et al. | 606/230 |
| 5,468,253 A | 11/1995 | Bezwada et al. | 606/230 |
| 5,554,170 A | 9/1996 | Roby et al. | 606/230 |
| 5,713,920 A | 2/1998 | Bezwada et al. | 606/230 |

FOREIGN PATENT DOCUMENTS

| | | | |
|---|---|---|---|
| EP | 618250 A1 | 3/1994 | C08G/63/91 |
| EP | 697427 A2 | 7/1995 | C08G/63/08 |
| EP | 712880 A2 | 11/1995 | C08G/81/00 |
| EP | 737703 A2 | 4/1996 | C08G/63/664 |

Primary Examiner—Patricia A. Short
(74) Attorney, Agent, or Firm—Leigh P. Gregory

(57) ABSTRACT

The present invention is directed to crystalline, absorbable block/segmented copolymers which are the reaction product of a linear prepolymer which is a polytrimethylene dicarboxylate of succinic, glutaric, or adipic acid and either glycolide, 1-lactide, or mixtures thereof. Preferably the prepolymer is preliminarily end-grafted with a further monomer such as trimethylene carbonate or ε-caprolactone. The crystalline copolymers of this invention are tailored for fabrication into several forms of absorbable biomedical devices including monofilament sutures.

33 Claims, No Drawings

COPOLYESTERS WITH MINIMIZED HYDROLYTIC INSTABILITY AND CRYSTALLINE ABSORBABLE COPOLYMERS THEREOF

This is a divisional of application Ser. No. 09/420,767 filed on Oct. 19, 1999, now U.S. Pat. No. 6,255,408, which claimed the benefit of U.S. Provisional Application No. 60/107,503, filed Nov. 6, 1998.

BACKGROUND OF THE INVENTION

Since the successful development of the crystalline thermoplastic polyglycolide (PG) and 10/90 poly(1-lactide-co-glycolide) (PLG) as absorbable suture materials, there have been many successful attempts to prepare a number of new absorbable, crystalline homopolymers as well as segmented and block copolymers by ring-opening or condensation polymerization for use in a variety of biomedical and pharmaceutical applications Meanwhile, a few monomers have been considered to be the necessary precursors for the production of truly absorbable polyesters by ring-opening polymerization. These monomers are glycolide, lactide, and p-dioxanone Of the condensation-type absorbable polymers, only certain polyanhydrides and polyalkylene oxalates have been recognized as crystalline thermoplastic materials. Most pertinent to the copolymers, subject of this invention, are crystalline absorbable thermoplastic copolymers made by end-grafting low Tg (glass transition temperature) absorbable, so-called "soft" blocks or segments with relatively high Tg crystallizable, chains usually denoted as "hard" blocks or segments. See, for example, U.S Pat Nos. 5,554,170; 5,431,679; 5,403,347, 5,236,444; 5,133,739; and 4,429,080. The terms segment and block are used to denote relatively short and long structures of repeat units in the polymeric chain, respectively In designing the soft segments, or blocks, of the prior art, polar cyclic monomers have been used as precursors to produce these moieties in essentially amorphous, highly flexible form by ring-opening polymerization However, most of the segments or blocks of the prior art were made to contain small amounts of hydrolytically labile ester linkages derived from glycolide or p-dioxanone to attain a timely absorption of the entire block/segmented copolymer. And in commercial products having the hard-soft segment/block molecular architecture, the hard component of the copolymers have been made primarily or totally of glycolide-derived chains. Unfortunately, having the labile linkage in the soft segments or blocks not only facilitates their absorption, but also causes a premature or early and sudden reduction in the molecular weight of the load-bearing long chains and, hence, an early reduction in breaking strength and related physicomechanical properties of implants based on these copolymers. This provided the incentive to develop the new, linear, semi-crystalline block/segmented copolymers, subject of this invention, wherein the soft blocks or segments are designed to comprise less polar chain sequences formed by step-growth polymerization of acyclic precursors, which are not expected to be absorbable as homopolymers, in order to minimize the hydrolytic instability of the entire block/segmented systems having the more traditional hard components. Accordingly, one aspect of this invention deals with block/segmented copolymers having the soft segment made by step-growth polymerization of an alkane diol and diester which are not known as the common precursors of absorbable homopolymers. In another aspect of this invention, the soft segment/block is made by further end-grafting the aforementioned step-growth alkylene dicarboxylate prepolymer with a cyclic ester and/or carbonate other than those known to provide labile ester linkages such as glycolide and p-dioxane.

SUMMARY OF THE INVENTION

The present invention is directed to a crystalline, absorbable block/segmented copolymer which is the reaction product of (a) a linear prepolymer comprising a polyalkylene dicarboxylate, preferably a polytrimethylene of one or more acids selected from the group consisting of succinic acid, glutaric acid, sebacic acid and adipic acid; and (b) a monomer selected from the group consisting of glycolide, lactide, and mixtures thereof Preferably, prior to reaction with the glycolide, lactide or mixtures thereof, the prepolymer is end-grafted with a monomer selected from the group consisting of aliphatic carbonate, cyclic carbonate, caprolactone, and 1,5-dioxapan-2-one. Most preferably, the prepolymer is first end-grafted with trimethylene carbonate, $\epsilon$-caprolactone, or a mixture of the two With or without preliminary end-grafting, the polymer comprises from about 20% to about 80% by weight of the overall copolymer and preferably from about 30% to about 70% by weight.

It is preferred that the prepolymer is amorphous or that the prepolymer has a melting temperature at or below 50° C., most preferably at or below 37° C.

The copolymers of the present invention may be used in the production of a variety of bioabsorble medical devices. Certain types of the present copolymers are especially suited for forming monofilament sutures

DETAILED DESCRIPTION OF PREFERRED EMBODIMENTS

The present invention is directed to the design of segmented/block copolymeric chains to provide absorbable materials for the production of biomedical articles with controlled absorption and strength retention profiles. The copolymers of the present invention have an amorphous or low melting temperature phase that is based primarily on soft segments or blocks whose chains are essentially devoid of distinctly hydrolytically labile ester linkages and, hence, provide an overall minimized hydrolytic instability.

The present copolymers are defined as blocked or segmented because they are of the type having blocks or segments made from "hard" phase forming monomers and one or more blocks or segments made from "soft" phase forming monomers. Generally, the hard phase blocks or segments lend mechanical strength to the overall copolymer and the soft phase blocks or segments render the copolymer compliant. The term "block copolymer" typically refers to a copolymer having two or more blocks or long structures of repeat units such as the general form A-B, A-B-A, or $(A-B)_n$. A "segmented copolymer" is typically considered to be one with multiple relatively short structures such as a-b-a-b . . . or a-b-c-a-b . . . , where the a, b, and c are shorter than the A and B of the block copolymers. The present copolymers are referred to as "block/segmented copolymers" herein because they may contain a limited number of long blocks or several short segments per chain. These terms are intended to distinguish the present copolymers from random copolymers.

The copolymers of the present invention are formed by the copolymerization of a prepolymer, which will ultimately form the soft block or segments, with one or more monomers which will ultimately form the hard blocks or segments. The prepolymer of the present invention is, at least, a polyalkylene dicarboxylate, preferably a polytrimethylene dicarboxylate of glutaric, adipic, sebacic and/or succinic acid. More preferably, the polytrimethylene dicarboxylate is end-grafted with at least one or more monomers of the group a cyclic carbonate, ε-caprolactone, and 1,5-dioxapan-2-one. The preferred cyclic carbonate is trimethylene carbonate. Thus, in one preferred embodiment a polytrimethylene dicarboxylate of succinic acid is end-grafted with trimethylene carbonate. In another preferred embodiment a polytrimethylene dicarboxylate of succinic acid is end-grafted with a mixture of trimethylene carbonate and ε-caprolactone.

Generally, the soft block or segments must be incapable of crystallization between 25–50° C. and display a high degree of chain mobility at about room temperature. That is, preferably the prepolymer which will ultimately form the soft block is either amorphous or has a melting temperature of 50° C. or less. Most preferably, it is either amorphous or has a melting temperature of 37° C. or less. Optionally, the prepolymer is a liquid.

Attached to soft block or segments is one or more blocks or segments that are capable of crystallization under prevailing processing conditions to form the crystalline or hard component of the final copolymeric system. Preferably, hard components are composed primarily of repeat units derived from glycolide, lactide, or mixtures thereof. Optionally, minor co-repeat units (or sequences) in the hard segments are derived from trimethylene carbonate or ε-caprolactone.

Depending on the intended application of these copolymers, the hard and soft blocks or segments may comprise from about 20% to about 80% by weight, each, of the entire system. More preferably, the soft components may comprise from about 30% to about 70% by weight and the hard components may comprise from about 30% to about 70% by weight.

Generally, the copolymers of the present invention may be prepared as follows, although, as noted above, other monomers are also within the scope of the present invention. The prepolymer is formed by a preliminary polymerization of 1,3-propanediol with, for example, diethyl succinate in the presence of an organometallic catalyst, such as stannous octoate and dibutyl tin oxide, using standard polycondensation conditions, entailing first-stage condensation at 120–220° C. under atmospheric pressure followed by post-polymerization under reduced pressure at temperatures ranging between 220–250° C. The resulting polycondensate is then, preferably, end-grafted with an equal weight of trimethylene carbonate and ε-caprolactone under by ring-opening polymerization to produce the prepolymer. The prepolymer is then further grafted with glycolide, a 95/5 mixture of glycolide and l-lactide, or a 5/95 mixture of glycolide and l-lactide to produce final crystalline copolymer of the present invention.

Trace amounts of the unreacted monomer are removed from the prepolymer by extraction or distillation under reduced pressure at a suitable temperature. The composition of the polymers is determined by NMR and IR. The polymer molecular weight and purity are determined in terms of inherent viscosity or gel-permeation chromatography (GPC), respectively. Thermal transitions are determined by differential scanning calorimetry. Melt-rheology of the polymer is evaluated using capillary rheometry.

For the Examples set forth below, the ground polymer was first dried to remove traces of moisture and unreacted monomer under reduced pressure at temperatures ranging between 40° C. and 110° C. Depending on the melting temperature (Tm) of the hard segment (block) of the polymer, melt-spinning (using a single screw extruded) can be achieved at temperatures ranging between 140–250° C. The extrudate is jet-stretched to attain the desired diameter and passed through a quench bath (cold air, nitrogen, or ice-water). The extrudate can be dried and drawn in a single or 2-stage process to attain a draw ratio of 4 to 8×. Fiber annealing may be pursued with or without tension before and/or after drawing to develop a required level of crystallinity and tensile properties.

For fibers made in accordance with the Examples set forth below, evaluations included (1) tensile properties evaluation of the fiber straight tensile strength, knot strength, elongation, and modulus (typically, these can vary between 50 and 110 Kpsi, 40 and 65 Kpsi, 20 and 80 percent and 100 to 600 Kpsi, respectively), (2) in vitro breaking strength retention during incubation in a phosphate buffer at 37° C. or 50° C. for a period of 3 to 56 days—the breaking strength is determined periodically using a universal tensile tester;

(3) in vivo breaking strength retention using a rat model where the suture is implanted subcutaneously for 1 to 10 weeks and individual lengths are explanted periodically to determine percent of retained breaking strength using a universal tensile tester—typically the percent breaking strength retention (depending on the suture composition) can vary between 30–90, 20–80, 0–70, 0–50, 0–40 and 0–20 at 1-, 2-, 3-, 6-, 8- and 10-week periods, respectively.

To determine the in vitro absorption profile, the sutures were incubated in a phosphate buffer at 37, 50, and 80° C. for 2 to 60 days and loss in mass was determined on individual samples periodically. For in vivo determination of the absorption profile and tissue reaction, segments of the suture were implanted in the rat gluteal muscle (or similarly large muscle). Muscle was then excised from a sacrificed rat at different time periods, sectioned and stained to determine the tissue reaction (using standard histopathological techniques) and absorption was measured in terms of percent change in cross-sectional area. Many of the sutures made in accordance with the present invention were found to absorb within a period ranging from six weeks to 30 months Specifically, an important aspect of the present invention is the production of compliant, absorbable monofilament sutures which can controllably retain an appreciable fraction of their initial in vivo breaking strength over a period of 1 to 10 weeks and absorb in 26 weeks to 30 months depending primarily on the composition and weight fraction of the soft and hard segments In another aspect, this invention is directed to the use of the polymers described in this invention for the production of extruded or molded films for use in barrier systems to prevent post-surgical adhesion or as compliant covers, sealants or barriers for burns and ulcers as well as other compromised/damaged tissues In another aspect, this invention is directed to the use of polymers for the production of nonwoven and particularly melt-blown fabrics for use in tissue repair, regeneration, and/or engineering In another aspect, this invention is directed to extruded tapes for use in restraining tissue or organs during surgical procedures. In another aspect, this invention is directed to the use of the polymers described herein for production of extruded catheters for use as transient conduits and microcellular foam with continuous porous structures for use in tissue engineering and in guiding the growth of nerve ends. Another aspect of this invention is directed to the use of the polymers to produce injection molded articles for use as barriers or plugs to aid the function of certain biomedical devices used in soft and hard tissues and which can be employed in repairing, augmenting, substituting bone or redirecting/assisting the functions of several types of tissue including bone, cartilage, and lung as well as vascular tissues and components of the gastrointestinal and urinogenital systems.

It is contemplated that it may be desirable to dye certain types of the several biomedical devices made of the copolymers subject of this invention in order to increase visibility in the surgical field.

The block or segmented copolymers of this invention can be formed into surgical articles using any known technique such as, for example, extrusion, molding, melt-blowing, spinning, and/or solvent casting. The copolymers can be used alone or blended with other absorbable compositions or in combination with nonabsorbable compositions. The copolymer can also be co-extruded with other absorbable or non-absorbable copolymers to form bicomponent fibers or films A wide variety of surgical articles or components thereof can be manufactured from the copolymers of this invention. These include, but are not limited to, clips and other fasteners, staples, sutures, pins, screws, prosthetic devices, bone and vascular plugs, wound dressings, suture pledgets, scaffolds for tissue adhesives, wound covers, scaffolds for tissue engineering, drug delivery devices, anastomosis rings, and other implantable devices, which can be solid, hollow, or micellular constructs. Fibers made from the copolymers of this invention can be knitted or woven with or without other fibers, either absorbable or nonabsorbable, to form meshes or fabrics. The compositions of this invention can be used as an absorbable coating for surgical devices, including sutures and stents. Preferably, however, the copolymers are spun into fibers to be used as sutures, either monofilament or multifilaments. The suture of the present invention may be attached to a surgical needle.

It is further within the scope of this invention to incorporate one or more medico-surgically useful substances into the copolymers and devices, subject of this invention, e.g., those which accelerate or beneficially modify the healing process when articles are applied to a surgical repair site. So, for example, sutures may carry therapeutic, antimicrobial, or growth reoulating agents, which can be released controllably at the repair site. Copolymers of this invention may also be used as the whole device or part of the device for housing radioactive materials associated with oncological procedures.

In order that those skilled in the art may be better able to practice the present invention, the following illustrations of the preparation of typical copolymers and their conversion to useful articles and subsequent characterization/testing and evaluation are provided.

EXAMPLE 1

Diethyl succinate (2.3 moles) was reacted with 1,3 propanediol (4 6 moles) in the presence of dibutyl tin oxide at a monomer to catalyst ratio of 25,000 to 1. The charge was heated in a dry reaction flask under argon at 220° C. for 5.5 hr., and then further reacted at 0.1 mm Hg for 30 hr. during which time the temperature was increased from ambient to 200° C. The resulting polysuccinate had a $M_w$ of 11,993, a $M_n$ of 7,396, and a polydispersity of 1.62 as measured by GPC.

EXAMPLE 2

Diethyl succinate (2.3 moles) was reacted with 1,3 propanediol (4.6 moles) in the presence of dibutyl tin oxide at a monomer to catalyst ratio of 25,000 to 1. The charge was heated in a dry reaction flask under argon at 220° C. for 5.5 hr., and then further reacted at 0.1 mm Hg for 36.5 hr during which time the temperature was increased from ambient to 200° C. The resulting polysuccinate had a $M_w$ of 8,033, a $M_n$ of 4,813, and a polydispersity of 1.67 as measured by GPC.

EXAMPLE 3

The polytrimethylene succinate of Example 1 was reacted with trimethylene carbonate (TMC) monomer at a weight ratio of 1 to 4. The charge was reacted in a dry flask under argon at 150° C. for 3 hr. and then 180° C. for 3 hr while stirring at 34 rpm. This prepolymer had a $M_w$ of 55,174, a $M_n$ of 29,031, and a polydispersity of 1.90 as measured by GPC. The polysuccinate/TMC prepolymer was reacted with glycolide at a weight ratio of 35 to 65. The charge was dried at 50° C. and 0.1 mm Hg for 30 min. and then reacted at 230° C. under argon for 1.5 hr. The inherent viscosity measured as a solution in hexafluoroisopropanol of the resulting polymer was 0.98, and the melting temperature measured by differential scanning calorimetiy was 213 8° C.

EXAMPLE 4

The polytrimethylene succinate of Example 2 was reacted with trimethylene carbonate (TMC) monomer at a weight ratio of 1 to 4 The charge was reacted in a dry flask under argon at 150° C. for 3 hr. and then 180° C. for 3 hr while stirring at 36 rpm. This prepolymer had a $M_w$ of 36,791, a $M_n$ of 25,240, and a polydispersity of 1.46 as measured by GPC. The polysuccinate/TMC prepolymer was reacted with glycolide at a weight ratio of 35 to 65; 0.1 % by weight D&C violet #2 was added to the charge. The charge was dried at 37° C. and 0.1 mm Hg for 80 min. and then at 50° C. and 0.1 mm Hg for 30 min. Once dry, the charge was reacted at 230° C. under argon for 15 hr. The inherent viscosity measured as a solution in hexafluoroisopropanol of the resulting polymer was 0.96, and the melting temperature measured by differential scanning calorimetry was 217.3° C.

EXAMPLE 5

The polytrimethylene succinate of Example 1 was reacted with trimethylene carbonate (TMC) monomer at a weight ratio of 1 to 1. The charge was reacted in a dry flask under argon at 150° C. for 3 hr and then 180° C. for 3 hr while stirring at 34 rpm. This prepolymer had a $M_w$ of 23,653, a $M_n$ of 12,633, and a polydispersity of 1.87 as measured by GPC. The polysuccinate/TMC prepolymer was reacted with glycolide at a weight ratio of 35 to 65. The charge was dried at 50° C. and 0.1 mm Hg for 30 min. and then reacted at 230° C. under argon for 1.5. hr The inherent viscosity measured as a solution in hexafluoroisopropanol of the resulting polymer was 0.68, and the melting temperature measured by differential scanning calorimetry was 216.6° C.

EXAMPLE 6

Extrusion of Copolymers of Examples 3, 4, and 5

These polymers were extruded using a Randcastle microtruder. Conditions for extrusion are given in Table I, below Corresponding extrudate properties are presented in Table II Inherent viscosity was measured as a solution in hexafluoroisopropanol; melting temperature and heat flow were measured using differential scanning calorimetry.

TABLE I

Extrusion Conditions

| Extrudate of Example No. | Zone 1 (° C.) | Zone 2 (° C.) | Zone 3 (° C.) | Die Zone (° C.) | Screw Speed (rpm) |
|---|---|---|---|---|---|
| 3 | 169 | 216 | 221 | 232 | 47.5 |
| 4 | 175 | 217 | 220 | 223 | 42.0 |
| 5 | 177 | 224 | 223 | 226 | 46.3 |

TABLE II

Extrudate Properties

| Extrudate of Example No. | d (mil) | Inherent Viscosity | $T_m$ (° C.) | ΔH (J/g) |
|---|---|---|---|---|
| 3 | 22.4 | 1.00 | 215.6 | 57.6 |
| 4 | 31.5 | 0.88 | 215.0 | 55.5 |
| 5 | 20.5 | 0.58 | 215.7 | 53.0 |

EXAMPLE 7

Extrusion of the Polymer of Example 4

Spinning was accomplished using an extruder from Hills Research and Development of Melbourne, Fla. The extruder was fitted with a 1.168 cc/rev zenith pump and a monofilament die. A quenching bath was positioned three inches below the die. The extruder screw zone temperatures were set at 178° C., 215° C., 212° C., and 206° C., and the screw speed was set at 40 rpm, the spin head temperature was set at 204° C. The spun fiber was wound onto a collection spool. The spun fiber had a diameter of 15.2 mil and a melting temperature of 213.3° C.

EXAMPLE 8

Fiber Drawing

Drawing was accomplished in one to three stages using heated glycerin baths. Drawing conditions are presented in Table III

TABLE III

Drawing Conditions

| | Stage 1 | | Stage 2 | | Stage 3 | |
|---|---|---|---|---|---|---|
| Fibers of Example No. | Draw Ratio | Temp (° C.) | Draw Ratio | Temp (° C.) | Draw Ratio | Temp (° C.) |
| 3 (as extruded in Ex. No. 6) | 7.5 | 50 | 1.4 | 85 | — | — |
| 4 (as extruded in Ex. No. 6) | 4 | 55 | 1.15 | 80 | — | — |
| 4 (as extruded in Ex. No. 7) | 4.7 | 45 | 1.1 | 80 | 1.8 | 90 |
| 5 (as extruded in Ex. No. 6) | 4.5 | 82 | — | — | — | — |

EXAMPLE 9

Fiber Mechanical and Thermal Properties

The drawn fibers were tested in tension at a strain rate of 25 mm/min. Fiber properties are presented in Table IV.

TABLE IV

Drawn Fiber Properties

| Fibers of Example No. | D (mil) | Strength (ksi) | Modulus (ksi) | % Elongation | $T_m$ (° C.) | ΔH (J/g) |
|---|---|---|---|---|---|---|
| 3 (as extruded in Ex. No. 6) | 9.8 ± 0.2 | 84 ± 3 | 397 ± 17 | 28.4 ± 0.8 | — | — |
| 4 (as extruded in Ex. No. 6) | 6.5 ± 0.6 | 78 ± 11 | 297 ± 75 | 36.6 ± 3.5 | 214.0 | 89.9 |
| 4 (as extruded in Ex. No. 7) | 8.6 ± 0.3 | 78 ± 3 | 250 ± 24 | 46.2 ± 3.9 | 214.3 | 51.0 |
| 5 (as extruded in Ex. No. 6) | 9.1 ± 03 | 66 ± 6 | 206 ± 21 | 54.5 ± 10.3 | — | — |

EXAMPLE 10

In Vitro Evaluation of Monofilament Sutures

Selected monofilaments were incubated in phosphate buffer (pH=7.4) at 37° C. for up to six weeks. The buffer was prepared as follows. Potassium phosphate, monobasic, (5.2 g) was dissolved in 190 ml distilled water Potassium phosphate, dibasic, (28.2 g) was dissolved in 810 ml distilled water. The two solutions were mixed together with 1000 ml distilled water, and the pH of the final solution was adjusted to 7.4. Sodium azide was added to the buffer solution at a final concentration of 0.05%. Monofilaments were tested in tension at a rate of 25 mm/min on a weekly basis to monitor the fiber breaking strength retention (BSR). In vitro study results are presented in Table V

TABLE V

In vitro Breaking Strength Retention

| Incubation Time (days) | Diameter (mils) | Strength (ksi) | Modulus (ksi) | % Elongation | Load at Break (lb) | % BSR |
|---|---|---|---|---|---|---|
| Fibers Made in Accordance with Examples 3 and 6 | | | | | | |
| 0 | 9.8 ± 0.2 | 84.0 ± 2.9 | 397.2 ± 17.0 | 28.4 ± 0.8 | 6.3 ± 0.4 | 100 |
| 7 | 9.5 ± 0.0 | 68.9 ± 20.6 | 219.4 ± 22.3 | 45.5 ± 9.5 | 4.8 ± 1.4 | 81.9 |
| 14 | 9.6 ± 0.4 | 63.4 ± 18.7 | 187.6 ± 48.0 | 46.8 ± 12.0 | 4.5 ± 1.4 | 75.4 |
| 21 | 9.7 ± 0.2 | 48.4 ± 9.0 | 160.5 ± 57.3 | 39.5 ± 9.4 | 3.5 ± 0.6 | 57.6 |
| 28 | 9.5 ± 0.6 | 32.2 ± 4.8 | 128.8 ± 15.9 | 25.9 ± 3.4 | 2.3 ± 0.4 | 38.4 |
| 35 | 10.1 ± 0.9 | 19.3 ± 7.4 | 91.7 ± 24.3 | 16.8 ± 3.2 | 1.5 ± 0.4 | 22.9 |

TABLE V-continued

In vitro Breaking Strength Retention

| Incubation Time (days) | Diameter (mils) | Strength (ksi) | Modulus (ksi) | % Elongation | Load at Break (lb) | % BSR |
|---|---|---|---|---|---|---|
| Fibers Made in Accordance with Examples 4 and 7 | | | | | | |
| 0 | 9.2 ± 0.2 | 68.7 ± 3.0 | 192.1 ± 17.1 | 54.5 ± 2.7 | 4.6 ± 0.2 | 100 |
| 7 | 9.2 ± 0.2 | 60.3 ± 3.1 | 167.3 ± 12.2 | 59.1 ± 2.0 | 4.0 ± 0.1 | 87.8 |
| 14 | 9.5 ± 0.6 | 47.5 ± 4.1 | 136.2 ± 27.7 | 46.8 ± 3.8 | 3.3 ± 0.2 | 69.1 |
| 21 | 9.5 ± 0.3 | 25.2 ± 2.9 | 125.1 ± 19.6 | 26.3 ± 2.3 | 1.8 ± 0.2 | 36.6 |
| 28 | 9.5 ± 0.5 | 10.8 ± 3.4 | 68.3 ± 6.7 | 12.8 ± 3.4 | 0.8 ± 0.2 | 15.7 |
| 35 | 9.6 ± 0.2 | 4.3 ± 0.5 | 51.8 ± 5.2 | 6.1 ± 0.7 | 0.3 ± 0.03 | 6.3 |
| 42 | 9.5 ± 0.3 | 3.0 ± 0.6 | 26.5 ± 1.8 | 7.2 ± 1.1 | 0.2 ± 0.04 | 4.2 |
| Fibers Made in Accordance with Examples 4 and 6 | | | | | | |
| 0 | 9.1 ± 0.3 | 65.8 ± 5.8 | 205.9 ± 21.3 | 54.5 ± 10.3 | 4.3 ± 0.5 | 100 |
| 7 | 10.7 ± 0.9 | 47.1 ± 5.0 | 110.8 ± 26.1 | 64.9 ± 6.4 | 4.2 ± 0.4 | 97.7 |
| 14 | 11.2 ± 1.4 | 32.3 ± 5.7 | 86.4 ± 19.9 | 52.0 ± 7.8 | 3.1 ± 0.2 | 72.1 |
| 21 | 11.6 ± 1.1 | 23.7 ± 4.9 | 67.9 ± 16.8 | 36.4 ± 2.3 | 2.5 ± 0.3 | 58.1 |
| 28 | 12.0 ± 1.1 | 9.3 ± 0.9 | 39.2 ± 3.7 | 19.8 ± 2.5 | 1.0 ± 0.1 | 23.3 |

EXAMPLE 11

In Vivo Evaluation of Monofilament Sutures

Monofilaments made in accordance with the present invention were implanted in the backs of Sprague Dawley rats to determine the breaking strength retention of the fiber after several weeks in vivo exposure. Rats were premedicated, anesthetized, and prepped for surgery. Incisions were made 2 cm lateral to the dorsal midline and a subcutaneous pocket was created by blunt dissection. Two nine inch lengths of monofilament were implanted in each pocket to give a total of four fibers per rat. Rats were euthanized in a carbon monoxide pre-charged chamber at pre-determined time points, the suture was retrieved from their backs, and tensile tests were conducted on the harvested material Results of this study are presented in Table VI.

TABLE VI

In vivo Breaking Strength Retention

| Implant Time (days) | Diameter (mil) | Maximum Load (lb) | % BSR | η | $T_m$ (° C.) | ΔH (J/g) |
|---|---|---|---|---|---|---|
| Fibers Made in Accordance with Example Nos. 3 and 6 | | | | | | |
| 0 | 9.1 ± 00 | 4.71 ± 0.60 | 100 | 0.88 | 214.0 | 52.6 |
| 7 | 11.7 ± 0.7 | 4.04 ± 1.23 | 85.7 | 0.86 | 214.3 | 53.8 |
| 14 | 10.6 ± 0.4 | 4.12* | — | 0.75 | 214.9 | 64.3 |
| 21 | 10.7 | 3.99 ± 0.33 | 84.6 | 0.63 | 215.6 | 76.8 |
| Fibers Made in Accordance with Example Nos 4 and 7 | | | | | | |
| 0 | 8.5 ± 0.5 | 5.1 ± 0.5 | 100 | 0.74 | 214.2 | 61.8 |
| 15 | 10.1 ± 0.4 | 4.1 ± 0.2 | 80.4 | 0.53 | 215.4 | 59.0 |
| 23 | 10.8 ± 0.6 | 1.8 ± 0.1 | 35.3 | 0.42 | 215.0 | 59.5 |
| 28 | 10.0 ± 0.2 | 1.4 ± 0.1 | 27.5 | 0.35 | 213.5 | 60.6 |
| 35 | 9.6 ± 0.3 | 0.7 ± 0.1** | 13.7 | — | — | — |
| Fibers Made in Accordance with Example Nos. 4 and 6 | | | | | | |
| 0 | 11.3 ± 0.4 | 6.0 ± 0.5 | 100 | 0.62 | 213.6 | 58.2 |
| 7 | 13.4 ± 0.9 | 2.6 ± 0.7 | 43.3 | 0.56 | 214.2 | 65.3 |
| 14 | 13.5 ± 0.3 | 4.3 ± 0.3** | 71.7 | 0.59 | 213.8 | 56.1 |
| 21 | 15.0 | 2.6* | 43.3 | 0.47 | 214.0 | 68.7 |

*Only 1 sample testable
**Only 2 samples testable.

Obviously, other modifications and variations of the present invention are possible in light of the above teachings. It is therefore to be understood that changes may be made in particular embodiments of the invention described which are within the full intended scope of the invention as defined by the claims.

What is claimed is:

1. A method for making a crystalline, absorbable block/segmented copolymer comprising the steps of:
    a) providing a primary linear prepolymer comprising a polyalkylene dicarboxylate of one or more acids selected from the group consisting of succinic acid, glutaric acid, sebacic acid and adipic acid, wherein the linear prepolymer is essentially amorphous;
    b) end-grafting the primary linear prepolymer with a cyclic monomer selected from the group consisting of cyclic carbonate, ε-caprolactone, 1,5-dioxapan-2-one, and mixtures thereof by ring opening polymerization thereby forming a secondary linear prepolymer; and
    c) end-grafting the secondary linear prepolymer with a cyclic monomer selected from the group consisting of glycolide, 1-lactide, and a mixtures thereof by ring opening polymerization.

2. The method set forth in claim 1 wherein the step of end-grafting the secondary linear prepolymer comprises end-grafting with a major portion of a cyclic monomer selected from the group consisting of glycolide, 1-lactide, and mixtures thereof and with a minor portion of a cyclic monomer selected from the group consisting of trimethylene carbonate and ε-caprolactone.

3. The method set forth in claim 1 wherein the polyalkylene dicarboxylate comprises polytrimethylene dicarboxylate.

4. The method set forth in claim 1 wherein the step of end-grafting the primary linear prepolymer with a cyclic monomer selected from the group consisting of cyclic carbonate, ε-caprolactone, 1,5-dioxapan-2-one, and mixtures thereof comprises end-grafting with a cyclic carbonate.

5. The method set forth in claim 4 wherein the cyclic carbonate comprises trimethylene carbonate.

6. The method set forth in claim 1 wherein the step of end-grafting the primary linear prepolymer with a cyclic monomer selected from the group consisting of cyclic carbonate, ε-caprolactone, 1,5-dioxapan-2-one, and mixtures thereof comprises end-grafting with a mixture of trimethylene carbonate and ε-caprolactone.

7. A crystalline, absorbable block/segmented copolymer comprising:
- a central segment having a melting temperature at or below 50° C. and derived from a linear prepolymer comprising a polyalkylene dicarboxylate of one or more acids selected from the group consisting of succinic acid, glutaric acid, sebacic acid, and adipic acid;
- terminal segments comprising moieties derived from a cyclic monomer selected from the group consisting of glycolide, 1-lactide, and mixtures thereof; and
- intermediate segments between and covalently bonded to each terminus of the linear prepolymer and the terminal segment moiety, the intermediate segments comprising moieties derived from a cyclic monomer selected from the group consisting of cyclic carbonate, ε-caprolactone, 1,5-dioxapan-2-one, and mixtures thereof.

8. The copolymer set forth in claim 7 wherein the terminal segments comprise a major portion of moieties derived from a cyclic monomer selected from the group consisting of glycolide, 1-lactide, a mixtures thereof, and a minor portion derived from a cyclic monomer selected from the group consisting of trimethylene carbonate and ε-caprolactone.

9. The copolymer set forth in claim 7 wherein the polyalkylene dicarboxylate comprises polytrimethylene dicarboxylate.

10. The copolymer set forth in claim 7 wherein the intermediate segments comprise moieties derived from a cyclic carbonate.

11. The copolymer set forth in claim 10 wherein the cyclic carbonate comprises trimethylene carbonate.

12. The copolymer set forth in claim 7 wherein the intermediate segment moieties derived from a mixture of trimethylene carbonate and ε-caprolactone.

13. The copolymer set forth in claim 7 wherein the central segment has a melting temperature at or below 37° C.

14. A surgical suture formed from the copolymer of claim 7.

15. The surgical suture set forth in claim 14 comprising a monofilament suture.

16. A surgical implant formed from the copolymer of claim 7.

17. The surgical implant set forth in claim 16 where said surgical implant comprises a clip.

18. A method for making a crystalline, absorbable block/segmented copolymer comprising the steps of:
- a) providing a primary linear prepolymer comprising a polyalkylene dicarboxylate of one or more acids selected from the group consisting of succinic acid, glutaric acid, sebacic acid and adipic acid, wherein the linear prepolymer has a melting temperature at or below 50° C.;
- b) end-grafting the primary linear prepolymer with a cyclic monomer selected from the group consisting of cyclic carbonate, ε-caprolactone, 1,5-dioxapan-2-one, and mixtures thereof by ring opening polymerization thereby forming a secondary linear prepolymer; and
- c) end-grafting the secondary linear prepolymer with a cyclic monomer selected from the group consisting of glycolide, 1-lactide, and a mixtures thereof by ring opening polymerization.

19. The method set forth in claim 18 wherein the step of end-grafting the secondary linear prepolymer comprises end-grafting with a major portion of a cyclic monomer selected from the group consisting of glycolide, 1-lactide, and mixtures thereof and with a minor portion of a cyclic monomer selected from the group consisting of trimethylene carbonate and ε-caprolactone.

20. The method set forth in claim 18 wherein the polyalkylene dicarboxylate comprises polytrimethylene dicarboxylate.

21. The method set forth in claim 18 wherein the step of end-grafting the primary linear prepolymer with a cyclic monomer selected from the group consisting of cyclic carbonate, ε-caprolactone, 1,5-dioxapan-2-one, and mixtures thereof comprises end-grafting with a cyclic carbonate.

22. The method set forth in claim 21 wherein the cyclic carbonate comprises trimethylene carbonate.

23. The method set forth in claim 18 wherein the step of end-grafting the primary linear prepolymer with a cyclic monomer selected from the group consisting of cyclic carbonate, ε-caprolactone, 1,5-dioxapan-2-one, and mixtures thereof comprises end-grafting with a mixture of trimethylene carbonate and ε-caprolactone.

24. A crystalline, absorbable block/segmented copolymer comprising:
- an essentially amorphous central segment derived from a linear prepolymer comprising a polyalkylene dicarboxylate of one or more acids selected from the group consisting of succinic acid, glutaric acid, sebacic acid, and adipic acid;
- terminal segments comprising moieties derived from a cyclic monomer selected from the group consisting of glycolide, 1-lactide, and mixtures thereof; and
- intermediate segments between and covalently bonded to each terminus of the linear prepolymer and the terminal segment moiety, the intermediate segments comprising moieties derived from a cyclic monomer selected from the group consisting of cyclic carbonate, ε-caprolactone, 1,5-dioxapan-2-one, and mixtures thereof.

25. The copolymer set forth in claim 24 wherein the terminal segments comprise a major portion of moieties derived from a cyclic monomer selected from the group consisting of glycolide, 1-lactide, a mixtures thereof, and a minor portion derived from a cyclic monomer selected from the group consisting of trimethylene carbonate and ε-caprolactone.

26. The copolymer set forth in claim 24 wherein the polyalkylene dicarboxylate comprises polytrimethylene dicarboxylate.

27. The copolymer set forth in claim 24 wherein the intermediate segments comprise moieties derived from a cyclic carbonate.

28. The copolymer set forth in claim 27 wherein the cyclic carbonate comprises trimethylene carbonate.

29. The copolymer set forth in claim 24 wherein the intermediate segment moieties derived from a mixture of trimethylene carbonate and ε-caprolactone.

30. A surgical suture formed from the copolymer of claim 24.

31. The surgical suture set forth in claim 30 comprising a monofilament suture.

32. A surgical implant formed from the copolymer of claim 24.

33. The surgical implant set for thin claim 32 where said surgical implant comprises a clip.

* * * * *